(12) United States Patent
Mashita et al.

(10) Patent No.: US 12,203,904 B2
(45) Date of Patent: Jan. 21, 2025

(54) PERFORMANCE EVALUATION METHOD FOR ELASTIC MATERIAL

(71) Applicant: Sumitomo Rubber Industries, Ltd., Kobe (JP)

(72) Inventors: Ryo Mashita, Kobe (JP); Hiroyuki Kishimoto, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 366 days.

(21) Appl. No.: 17/752,584

(22) Filed: May 24, 2022

(65) Prior Publication Data

US 2022/0404253 A1 Dec. 22, 2022

(30) Foreign Application Priority Data

Jun. 14, 2021 (JP) .................. 2021-098755

(51) Int. Cl.
*G01N 3/06* (2006.01)
*G01N 3/08* (2006.01)
*G01N 3/22* (2006.01)
*G01N 3/56* (2006.01)
*G01N 11/14* (2006.01)
(Continued)

(52) U.S. Cl.
CPC .................. *G01N 3/56* (2013.01); *G01N 3/06* (2013.01); *G01N 3/08* (2013.01); *G01N 3/22* (2013.01); *G01N 11/142* (2013.01); *G01N 15/088* (2013.01); *G01N 23/046* (2013.01); *G01N 33/445* (2013.01); *G01N 2015/0846* (2013.01); *G01N 2203/006* (2013.01); *G01N 2203/0092* (2013.01); *G01N 2203/0647* (2013.01); *G01N 2223/419* (2013.01); *G01N 2223/627* (2013.01); *G01N 2223/648* (2013.01)

(58) Field of Classification Search
CPC .. G01N 3/06; G01N 3/08; G01N 3/22; G01N 3/56; G01N 11/142; G01N 23/046; G01N 33/445; G01N 2015/0846; G01N 2203/006; G01N 2203/0075; G01N 2203/0092; G01N 2203/0647; G01N 2223/419; G01N 2223/627; G01N 2223/648
See application file for complete search history.

(56) References Cited

FOREIGN PATENT DOCUMENTS

JP   2005-308447 A   11/2005
JP   2017-83182 A    5/2017
(Continued)

OTHER PUBLICATIONS

Translation for JP 2020-008282 A, filed Jan. 16, 2020 (Year: 2020).*
(Continued)

*Primary Examiner* — Mark R Gaworecki
(74) *Attorney, Agent, or Firm* — Birch, Stewart, Kolasch & Birch, LLP

(57) ABSTRACT

A performance evaluation method for elastic material including rubber or elastomer, the method includes a step of applying a strain to a test piece made of the elastic material to form at least one void inside the test piece, a step of obtaining projected images of the test piece by irradiating the test piece with X-rays at a plurality of times after the at least one void is formed, and a step of obtaining a volume change of the at least one void between the plurality of times based on the projected images, as one of indexes of performance.

13 Claims, 5 Drawing Sheets

(51) Int. Cl.
*G01N 15/08* (2006.01)
*G01N 23/046* (2018.01)
*G01N 33/00* (2006.01)
*G01N 33/44* (2006.01)

(56) References Cited

FOREIGN PATENT DOCUMENTS

| JP | 2020-8282 A | | 1/2020 |
|----|-------------|---|--------|
| JP | 2020008282 A | * | 1/2020 |

OTHER PUBLICATIONS

Extended European Search Report for European Application No. 22155783.8, dated Jul. 18, 2022.
Federico et al., "Cavitation in thermoplastic-reinforced rubber composites upon cyclic testing: Multiscale characterization and modelling," Polymer, vol. 211, 2020, 13 pages total.

* cited by examiner

PERFORMANCE EVALUATION METHOD FOR ELASTIC MATERIAL

RELATED APPLICATIONS

This application claims the benefit of foreign priority to Japanese Patent Application No. JP2021-098755, filed Jun. 14, 2021, which is incorporated by reference in its entirety.

FIELD OF THE INVENTION

The present disclosure relates to performance evaluation method for elastic material.

BACKGROUND OF THE INVENTION

Conventionally, as a method for evaluating the performance of an elastic material (for example, performance related to wear), a method of wearing an elastic material by an indoor wear tester such as a Ramborn wear tester has been proposed (e.g., Patent Document 1).

Patent Document

[Patent Document 1] Japanese Unexamined Patent Application Publication 2005-308447

SUMMARY OF THE INVENTION

Unfortunately, there has been a problem that the performance results evaluated by the above method are not match the performance results of the actual product using the elastic material.

The present disclosure has been made in view of the above circumstances, and has a major object to provide a method capable of predicting performance of an elastic material.

In one aspect of the present disclosure, 1. a performance evaluation method for elastic material including rubber or elastomer, the method includes a step of applying a strain to a test piece made of the elastic material to form at least one void inside the test piece, a step of obtaining projected images of the test piece by irradiating the test piece with X-rays at a plurality of times after the at least one void is formed, and a step of obtaining a volume change of the at least one void between the plurality of times based on the projected images, as one of indexes of performance.

DETAILED DESCRIPTRION OF THE INVENTION

Figure 1:
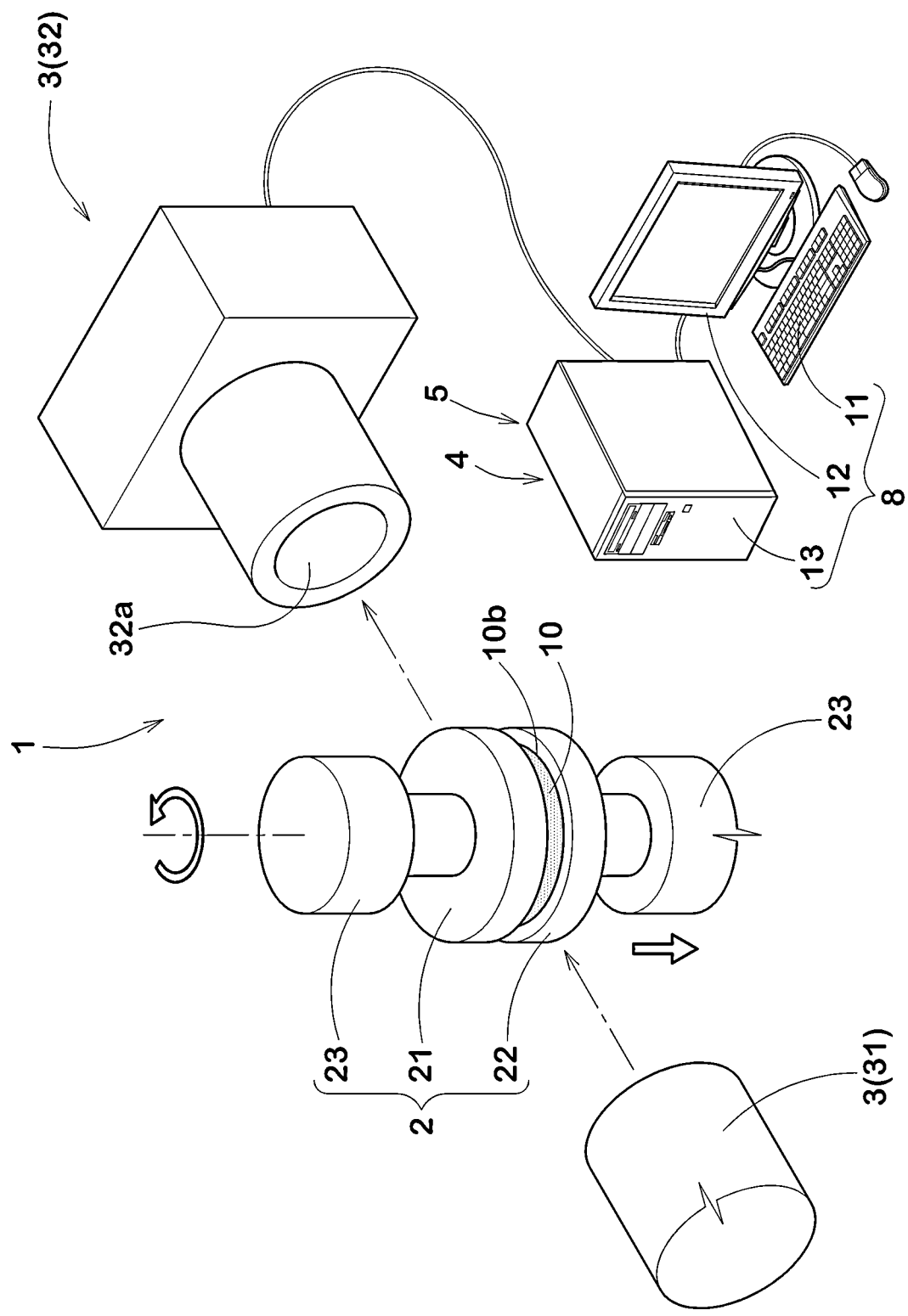
FIG. 1 is a perspective view of a performance evaluating system for elastic material in accordance with the present embodiment.

Hereinafter, one or more embodiments of the present disclosure will be described with reference to the drawings.

It should be noted that the drawings contain exaggerated expressions and expressions that differ from the dimensional ratio of the actual structure in order to help the understanding of the content of the disclosure. Further, throughout the embodiments, the same or common elements are given the same reference numerals, and duplicate explanations are omitted. Furthermore, note that the specific configurations shown in the embodiments and drawings are for understanding the contents of the present disclosure, and the present disclosure is not limited to the specific configurations shown in the drawings.

In the performance evaluation method for elastic material in accordance with the present embodiment (hereinafter, may be simply referred to as "performance evaluation method"), performance of an elastic material including rubber or elastomer can be evaluated.

[Elastic Material]

The elastic material can be selected as appropriate. As an example of the elastic material of the present embodiment includes rubber obtained using one or more kinds of conjugated diene compounds. Further, as rubber (an elastic material), for example, a rubber for tires can be selected. As an example of the performance evaluated by the method of the present embodiment, the performance related to wear (e.g., wear resistance performance) can be selected.

[Performance Evaluation System for Elastic Material]

As the performance evaluation method of the present embodiment, a performance evaluation system for elastic material (hereinafter, may be simply referred to as "performance evaluation system") 1 can be used. FIG. 1 illustrates a perspective view of the performance evaluation system 1 in accordance with the present embodiment.

The performance evaluation system 1 is for evaluating performance of elastic material. The performance evaluation system 1 according to the present embodiment includes a strain applying device 2, an imaging unit 3, a volume change obtaining unit 4, and an evaluation unit 5.

[Strain Applying Device]

The strain applying device 2 according to the present embodiment is for applying a strain to a test piece 10 made of an elastic material. The strain applying device 2 according to the present embodiment includes a pair of jigs 21 and 22 to which the test piece 10 is fixed, and drive units 23 that relatively moves the jigs 21 and 22 to distort the test piece 10.

The drive units 23, under a condition that one of the jigs 21 is fixed, move the other one of the jigs 22 in a direction that the jigs 21 and 22 are separated from one another. The drive units 23 according to the present embodiment move the other one of the jigs 22 in the axial direction of the test piece 10 which has a columnar shape. Thus, the test piece 10 is stretched in the axial direction and receives a strain.

The strain or the load that applies to the test piece 10 is measured using a load cell (not illustrated) and the like. The position and format of the load cell may be arbitrary. Using such a strain applying device 2, a predetermined strain or load can be applied to the test piece 10. The drive units 23 according to the present embodiment can also rotate the test piece 10 as well as the jigs 21 and 22 around the central axis of the test piece 10.

[Imaging Unit]

The imaging unit 3 according to the present embodiment can obtain projected images of the test piece 10 by irradiating X-rays to the test piece 10 being strained. The imaging unit 3 according to the present embodiment includes an X-ray tube 31 that irradiates X-rays and a detector 32 that detects X-rays and converts them into electrical signals. The detector 32 includes a phosphor 32a for converting X-rays into visible light. The imaging unit 3 can obtain projected images of the test piece 10 over the entire circumference by taking multiple projected images with the test piece 10 while the test piece is rotated around the central axis.

[Volume Change Obtaining Unit/Evaluation Unit]

Figure 2:
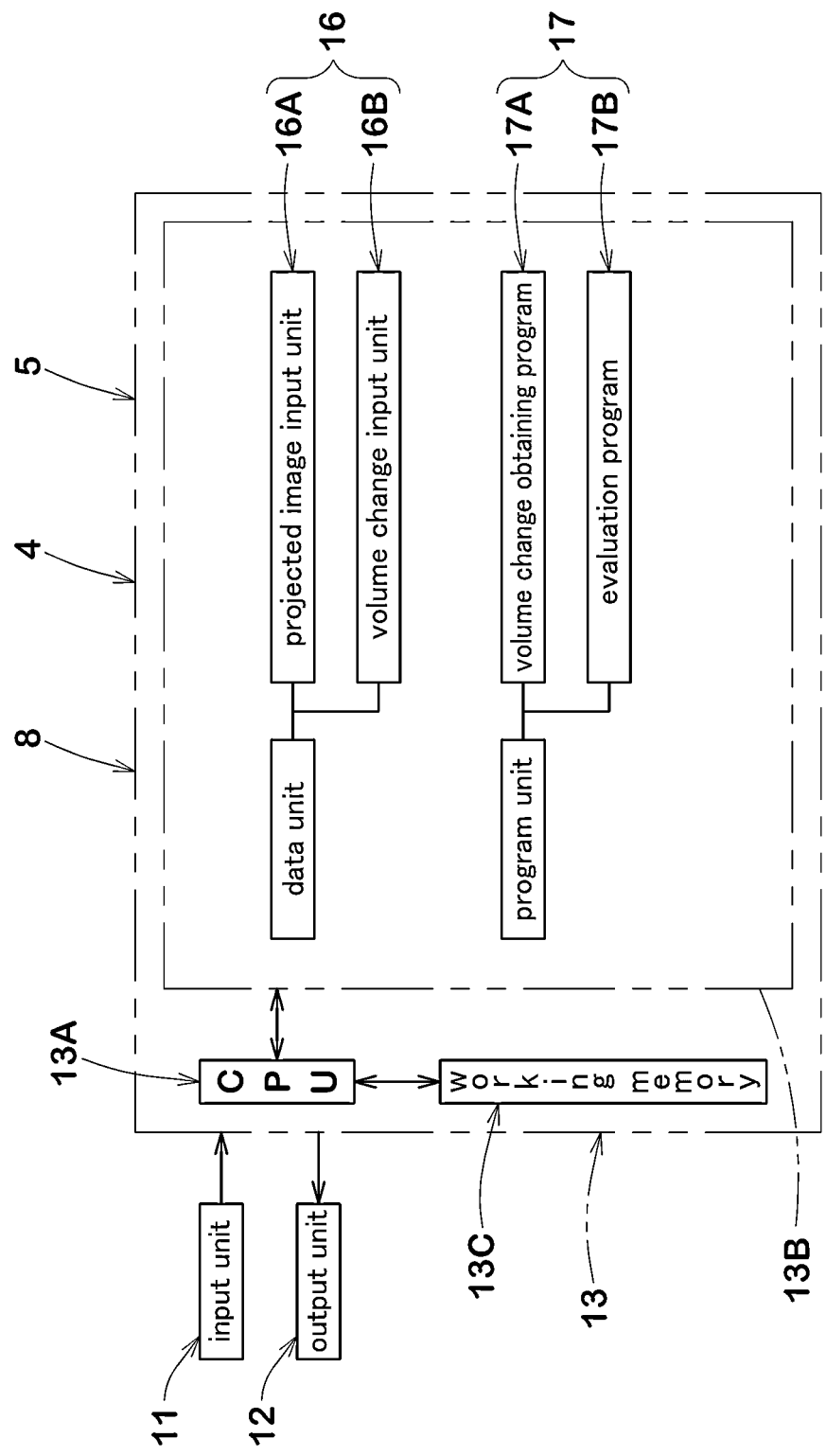
FIG. 2 is a block diagram of a computer.

In the present embodiment, the volume change obtaining unit 4 and the evaluation unit 5 are configured as components of a computer 8. FIG. 2 illustrates a block diagram of the computer 8 in accordance with the present embodiment.

The computer 8 according to the present embodiment includes an input unit 11 as an input device, an output unit 12 as an output device, and an arithmetic processing unit 13.

For the input unit 11, a keyboard or mouse may be used, for example. For the output unit 12, a display device or printer may be used, for example. The arithmetic processing unit 13 may be configured to include a central processing unit (CPU) 13A which performs various operations, a storage unit 13B for storing data, programs, etc., and a working memory 13C.

The storage unit 13B, for example, is a device which includes a non-volatile information storage device including magnetic disks, optical disks, SSDs, etc. The storage unit 13B works as a data unit 16 and a program unit 17.

In the present embodiment, the data unit 16 includes a projected image input unit 16A and a volume change input unit 16B. The data input to these will be explained in the processing procedures of the performance evaluation method described later.

In the present embodiment, the program unit 17 is configured as a computer program. The program unit 17 according to the present embodiment includes a volume change obtaining program 17A and an evaluation program 17B. The volume change obtaining program 17A and an evaluation program 17B can be executed by the central processing unit 13A to make the computer 8 function as the volume change obtaining unit 4 and the evaluation unit 7, respectively. These functions are explained in the processing procedures of the performance evaluation method described later.

[Performance Evaluation Method for Elastic Material]

Figure 3:
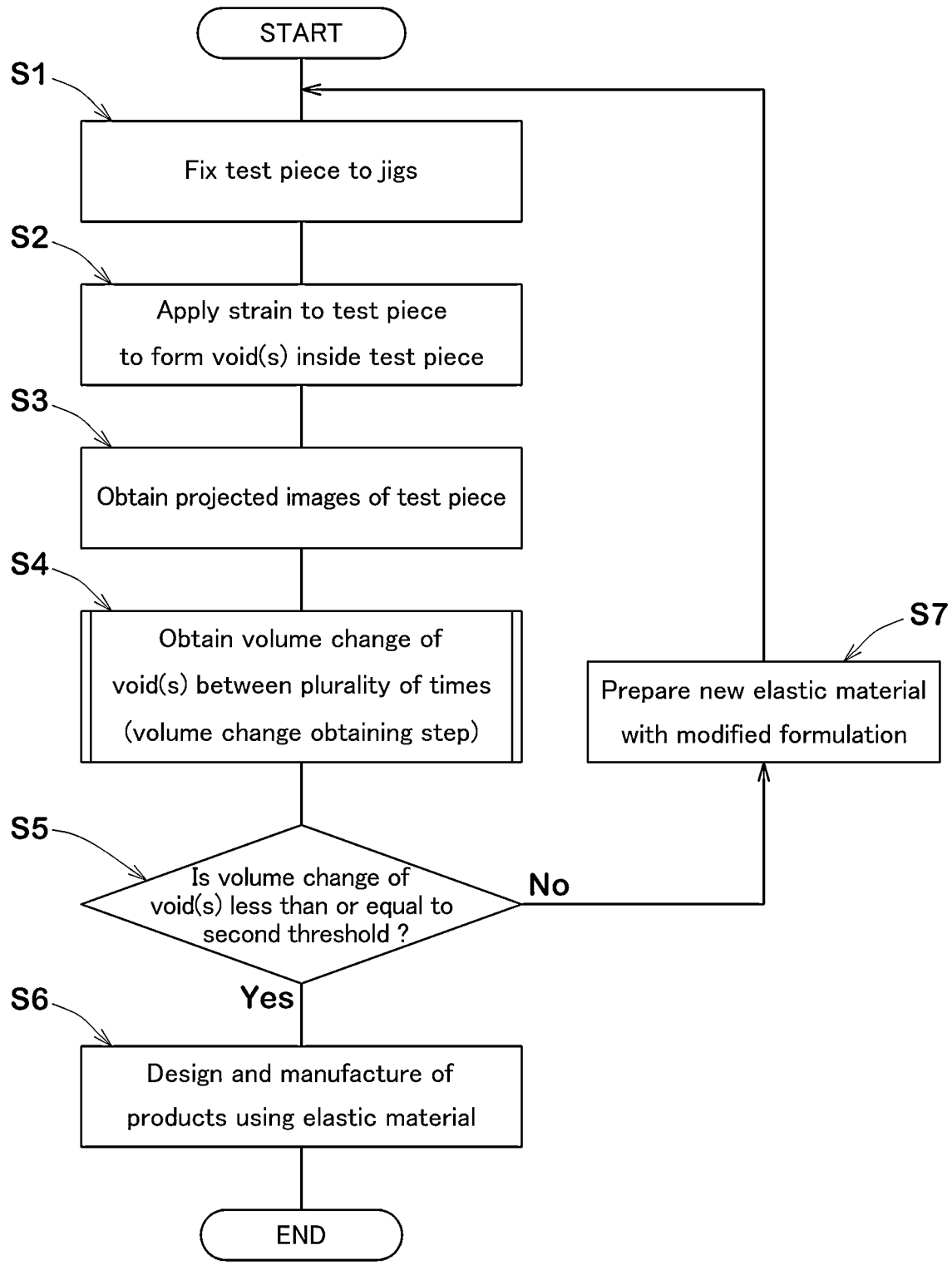
FIG. 3 is a flowchart showing processing procedures of a performance evaluating method for the elastic material in accordance with the present embodiment.

Next, the processing procedures of the performance evaluation method of the present embodiment will be explained. FIG. 3 is a flowchart showing the processing procedures of the performance evaluation method for elastic material of the present embodiment.

[Process of Fixing Test Piece]

In the performance evaluation method of the present embodiment, first, the test piece 10 is fixed to the jigs 21 and 22 as shown in FIG. 1 (step S1). In the present embodiment, the above-mentioned elastic material having a uniform density distribution is used for the test piece 10. The test piece 10 is formed in a columnar shape same as the Patent Document, Japanese Unexamined Patent Application Publication 2017-83182. The details of the test piece 10 and the procedures for fixing the test piece 10 to the jigs 21 and 22 are as described in Patent Document 1, which is incorporated by reference.

[Forming Void]

Next, in the performance evaluation method according to the present embodiment, a strain is applied to the test piece 10 to form at least one void inside the test piece 10 (step S2). In step S2, the jigs 21 and 22 of the strain applying device 2 are relatively moved in the axial direction of the columnar test piece 10 in the direction away from each other using the drive units 23 of the strain applying device 2. Thus, due to step S2, the test piece 10 is stretched so that the test piece 10 receives a strain.

In step S2 according to the present embodiment, since the test piece 10 is strained, local stress concentration occurs inside the test piece 10, and then the internal structure of the elastic material (bonding of molecular chains) is partially destroyed. As a result, one or more voids 15 (shown in FIGS. 4A and 4B) are formed inside the test piece 10. Here, "void" is defined as a portion where the density of the elastic material after being strained is from 0.0 to 0.1, when assuming that the average density of the elastic material before being strained is 1.0.

In step S2 according to the present embodiment, a tensile strain is applied to the test piece 10, for example. Thus, one or more voids 15 can be generated efficiently in the elastic material (the test piece 10) as compared to the case where other strains, e.g., compressive strain and shear strain, are applied.

In step S2, it is preferable that the strain given to the test piece 10 reaches a predetermined first threshold value. This may give the test piece 10 a certain strain (the first threshold value), so that a quantitative performance evaluation can be performed. The first threshold value (strain) is calculated that a displacement of the strained test piece 10 (the displacement of the test piece 10 from before receiving a strain) is divided by the axial length of the test piece 10 before receiving the strain (a reference length in the extension direction of the test piece 10). In the present embodiment, the first threshold value is set to 0.2.

The first threshold value may be appropriately set according to the rigidity of the elastic material, the performance to be evaluated, and the like. The first threshold is preferably equal to or more than 0.2. By setting the first threshold to 0.2 or more, one or more voids 15 (shown in FIGS. 4A and 4B) necessary for evaluating the performance of the elastic material can be formed inside the test piece 10 (elastic material). On the other hand, when the first threshold value becomes large, new voids (not shown) formed by connecting adjacent voids 15 and 15 become larger than necessary, which may make it difficult to evaluate the performance of elastic materials. From this point of view, the first threshold is preferably equal to or less than 1.0.

In the present embodiment, after the strain reaches the first threshold value in step S2, the strain (the first threshold value) is maintained in the subsequent step S3.

[Imaging Step]

Next, in the performance evaluation method according to the present embodiment, as shown in FIG. 1, the strained test piece 10 is irradiated with X-rays, and projected images of the test piece 10 are obtained (step S3). In step S3 according to the present embodiment, projected images of the test piece 10 are obtained at a plurality of times after the at least one void is formed. Step S3 according to the present embodiment is performed using the computer tomography method.

In step S3 according to the present embodiment, first, as shown in FIG. 1, the test piece 10 is irradiated with X-rays from the X-ray tube 31. The X-rays pass through the test piece 10 and are detected by the detector 32. The detected X-rays are converted into electrical signals which are output to the computer 8. The computer 8 processes these electrical signals to obtain projected images of the test piece 10.

In step S3 according to the present embodiment, a plurality of projected images (rotation series images) is obtained by rotating the test piece 10 around the axial direction. The plurality of projected images (rotation series images) is reconstructed by computer tomography method in a step S41, which will be described later, to obtain a three-dimensional tomographic image of the test piece 10.

Figure 4A:
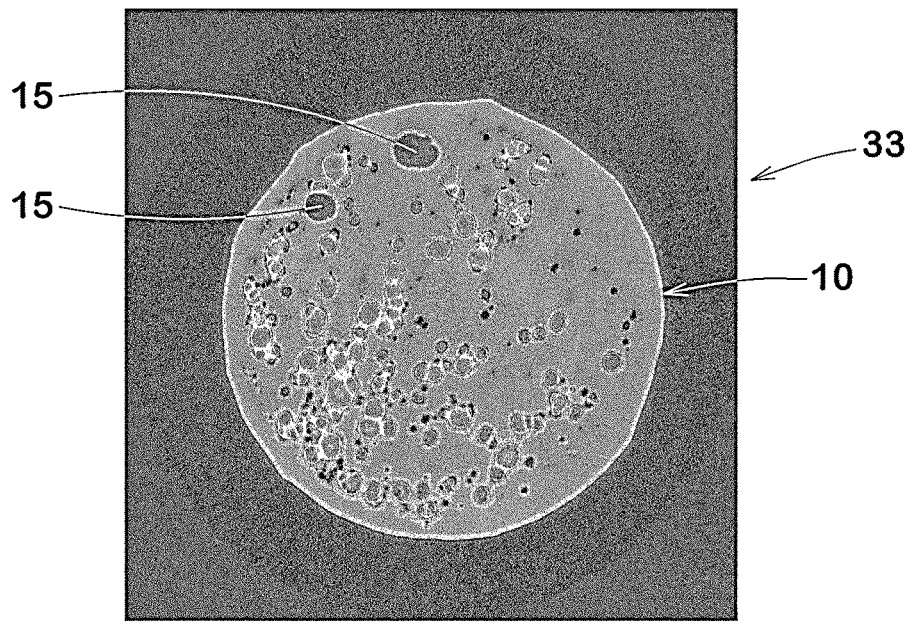
FIG. 4A is a tomographic image of a test piece obtained at the first time.
Figure 4B:
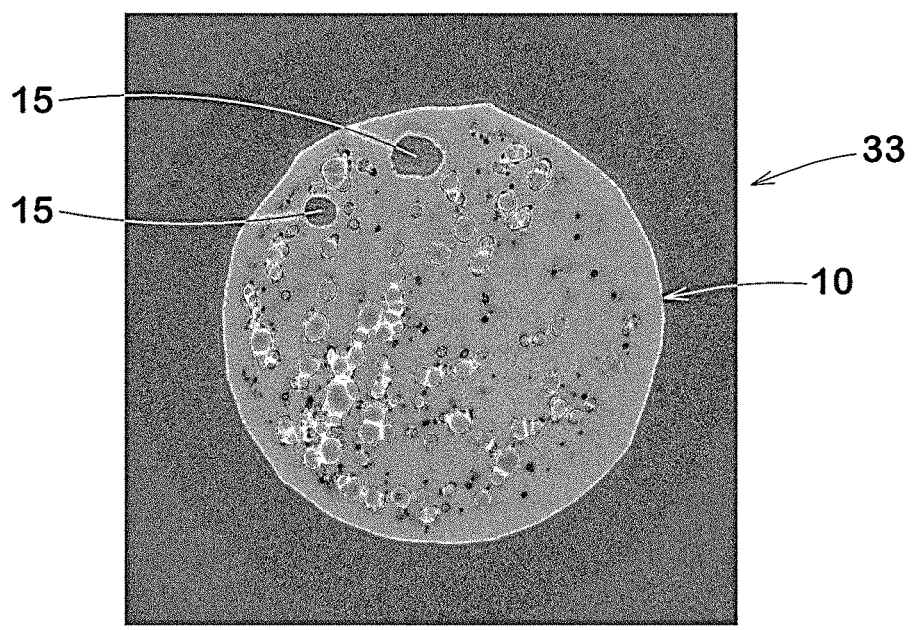
FIG. 4B is a tomographic image of the test piece obtained at the second time.

FIGS. 4A and 4B are tomographic images 33 of the test piece 10. These tomographic images 33 show a cut plane of the test piece 10 in a plane that intersects perpendicular to the axial direction of the test piece 10 shown in FIG. 1. The voids 15 are shown in black.

The brightness of X-rays can be set as appropriate. The brightness of X-rays may be greatly related to the S/N ratio of the X-ray scattering data. When the brightness of the X-rays becomes low, the signal intensity tends to be weaker than the X-ray statistical error, and it may be difficult to obtain data with a sufficiently high S/N ratio even if the measurement time is lengthened. From this point of view, the brightness of the X-rays (photons/s/mrad$^2$/mm$^2$/0.1%bw) is preferably equal to or more than $10^{10}$, more preferably equal to or more than $10^{12}$.

The decay time of the phosphor 32$a$ for converting X-rays to visible light can be set as appropriate. Similar to the above Patent Document (Japanese Unexamined Patent Application Publication 2017-83182), the decay time of the phosphor 32$a$ is preferably equal to or less than 100 ms, more preferably equal to or less than 50 ms, still further preferably equal to or less than 10 ms, in view of preventing the afterimage of the previously captured projected image from affecting the later captured projected image.

In step S3 according to the present embodiment, after one or more voids 15 are formed (in this example, after step S2 to form one or more voids 15), projected images of the test piece 10 are obtained at a plurality of times. As a result, in step S3, projected images of the test piece 10 in which the size (volume) of the voids 15 changes from moment to moment with progress of destroy of the internal structure (bonding of molecular chains) of the elastic material can be obtained at the respective times.

The plurality of times can be set as appropriate. The plurality of times according to the present embodiment includes a first time when the strain applied to the test piece 10 reaches the first threshold value. As a result, in step S3, a projected image of the test piece 10 immediately after being given a certain strain (the first threshold value) can be obtained, which means that the voids 15 required for performance evaluation have been formed.

In the present embodiment, the plurality of times includes a second time after a predetermined time has elapsed from the first time. The predetermined time (hereinafter referred to as "elapsed time") is not particularly limited as long as a projected image of the test piece 10 in which the size (volume) of the voids 15 has changed is obtained from the first time. Preferably, the elapsed time is set to 100 to 1200 seconds. When the elapsed time is equal to or more than 100 seconds, the volume of some voids 15 at the second time can be surely changed (larger) from the volume of the voids 15 at the first time. On the other hand, when the elapsed time is equal to or less than 1200 seconds, it is possible to prevent the time required to obtain the projected images from becoming longer than necessary. From this point of view, the elapsed time is preferably equal to or more than 400 seconds, and preferably equal to or less than 800 seconds. FIG. 4A is a tomographic image 33 of the test piece 10 obtained at the first time. FIG. 4B is a tomographic image 33 of the test piece 10 obtained at the second time.

In the present embodiment, the strain applied to the test piece 10 is maintained at the first threshold value during the time period that a plurality of projected images is obtained. As a result, the projected images of the test piece 10 in which the volume of the voids 15 changes based on a certain strain can be obtained at the plurality of times. The projected images of the test piece 10 obtained at the respective times (e.g., the first time and the second time) are input to the projected image input unit 16A (shown in FIG. 2) of the computer 8.

[Obtaining Volume Change]

Next, in the performance evaluation method according to the present embodiment, as one of indexes of performance, a volume change of the voids 15 between the plurality of times is obtained based on the projected images of the test piece 10 (volume change obtaining step S4).

Figure 5:
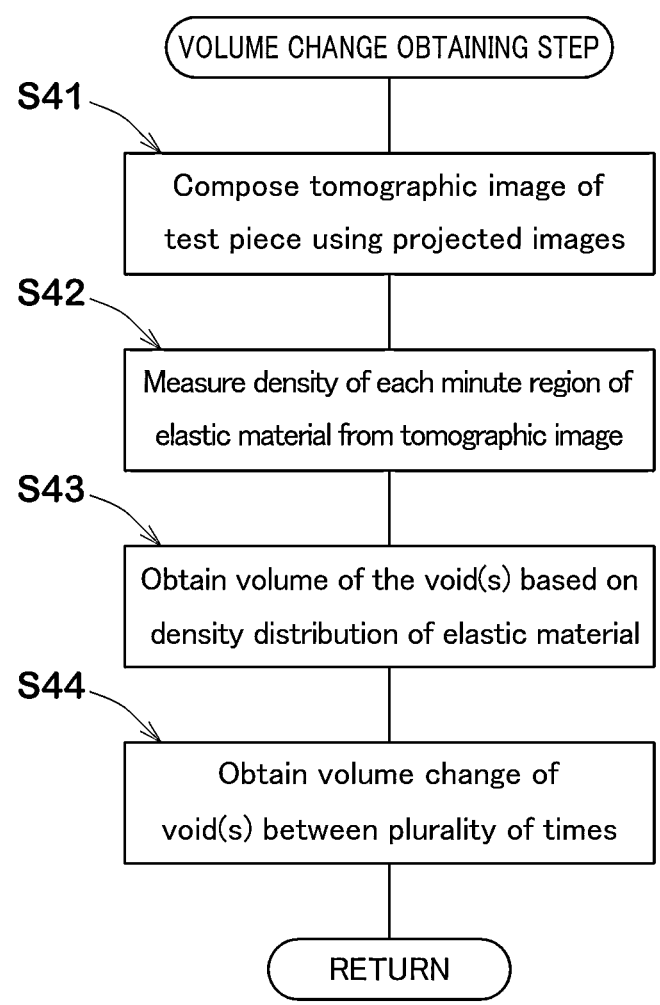
FIG. 5 is a flowchart showing the processing procedure of a step of obtaining a volume change.

In the volume change obtaining step S4 according to the present embodiment, first, as shown in FIG. 2, the projected images of the test piece 10 (not shown) input to the projected image input unit 16A and a volume change obtaining program 17A are read into the working memory 13C. Then, the volume change obtaining program 17A is executed by the arithmetic unit 13A, so that the computer 8 can function as the volume change obtaining unit 4 for obtaining the volume change of the voids 15 between the plurality of times. FIG. 5 illustrates a flowchart showing a processing procedure of the volume change obtaining step S4 according to the present embodiment.

[Composing Tomographic Image]

In the volume change obtaining step S4 according to the present embodiment, tomographic images 33 (shown in FIGS. 4A and 4B as an example) of the test piece 10 are composed using the projected images (step S41). In step S41 of the present embodiment, using the projected images of the test piece 10, a plurality of tomographic images 33 of the test piece 10 are obtained on an arbitrary plane that intersects perpendicularly to the axial direction of the test piece 10.

In the present embodiment, the tomographic images 33 are obtained at an arbitrary interval (for example, 5 to 30 μm) between one end (not illustrated) and the other end 10$b$ in the axial direction of the test piece 10 shown in FIG. 1. The number of tomographic images 33 composed in the present embodiment is 150 to 300.

In step S41 of the present embodiment, a plurality of tomographic images 33 are configured for each projected image obtained at the plurality of times (in this example, the first time and the second time). FIG. 4A shows a tomographic image 33 composed of the projected images obtained at the first time. FIG. 4B shows another tomographic image 33 composed of the projected images obtained at the second time.

[Measurement of Density]

Next, in the volume change obtaining step S4 according to the present embodiment, density of each minute region of the elastic material is measured from the tomographic images 33 (shown in FIGS. 4A and 4B) (step S42). In step S42 of the present embodiment, in the region of the test piece 10 displayed in each tomographic image 33, the brightness value is acquired for each minute region (e.g., each pixel) that constitutes each tomographic image 33. In the present embodiment, the brightness value is the lowest in the voids 15. Further, the higher the brightness value, the higher the density of the elastic material. Thus, a proportional relationship is established between the brightness value and the density.

Next, in step S42 of the present embodiment, the brightness value of the elastic material before receiving strain (i.e., the portion without the voids 15) is set to 1.0, and the brightness value in which the elastic material does not exist (the lowest brightness value) is set to 0. Then, the ratio of the brightness values of each minute region (each pixel in this example) is calculated. Each ratio of such a brightness value is defined as the normalized density (i.e., the ratio to the density of the elastic material before receiving strain).

[Obtaining Volume of Voids]

Next, in the volume change obtaining step S4 according to the present embodiment, the volumes of the voids 15 are obtained based on the density distribution of the elastic material (step S43). As mentioned above, the voids 15 in the elastic material are portions whose density is in a range of from 0.0 to 0.1 times of the density of the elastic material before the strain is applied. Thus, in step S43, the regions that are displayed by the minute regions (pixels) of each tomographic image 22 (shown in FIGS. 4A and 4B as an example) having the ratio of brightness values (normalized density) of 0.0 to 0.1 are detected as the voids 15. To detect the voids 15, commercially available image processing software (e.g., Photoshop (registered trademark) manufactured by Adobe) or the like can be used.

In step S43 according to the present embodiment, for the plurality of tomographic images 33 obtained at the first time, an area of the voids 15 detected in each tomographic image 33 and the interval at which the tomographic images 33 are obtained (for example, 5 to 30 μm) are multiplied to obtain the product. Then, each product of the plurality of tomographic images 33 is added together to obtain a total volume V0 of the voids 15 at the first time. Furthermore, in step S43, for the plurality of tomographic images 33 obtained at the second time, an area of the voids 15 detected in each tomographic image 33 and the interval at which the tomographic images 33 are obtained are multiplied to obtain the product. Then, each product of the plurality of tomographic images 33 is added together to obtain a total volume Vt of the voids 15 at the second time.

[Obtaining Volume Change]

Next, in the volume change obtaining step S4 according to the present embodiment, the volume change of the voids 15 between the plurality of times is obtained (step S44). In step S44 according to the present embodiment, a ratio Vt/V0 of the volume Vt of the voids 15 at the second time to the volume V0 of the voids 15 at the first time is specified as the volume change of the voids 15.

The volume change of the voids 15 indicates the increase (growth) of the volume of the voids 15 between the plurality of times (in this embodiment, between the first time and the second time). Through experiments, the inventors have found that there is a certain correlation between the volume change between the plurality of times and performance of elastic materials (in this example, the performance related to wear). In other words, it has been found that elastic materials with a small volume change is less likely to break the internal structure (bonding of molecular chains) and the performance of the elastic materials is good. Thus, in the performance evaluation method according to the present embodiment, it is possible to predict performance of elastic materials by obtaining the volume change of the voids as one of the indexes of the performance of the elastic material.

If the volume of the voids 15 at a time different from the first time and the second time (for example, the third time, etc.) is obtained, another volume change between those times (for example, between the second time and the third time) may be obtained. The volume change of the voids 15 is input to the volume change input unit 16B (shown in FIG. 2).

[Evaluation Step]

Next, in the performance evaluation method according to the present embodiment, performance of the elastic material is evaluated based on the volume change of the voids 15 (step S5).

In step S5 according to the present embodiment, as shown in FIG. 2, the volume change of the voids 15 input to the volume change input unit 16B and the evaluation program 17B are read into the working memory 13C. Then, the evaluation program 17B can be executed by the central processing unit 13A to make the computer 8 function as the evaluation unit 5 for evaluating the performance of the elastic material.

In step S5 according to the present embodiment, the volume change of the voids 15 is compared with a predetermined second threshold value. As mentioned above, an elastic material with a small volume change has good performance (in this embodiment, performance related to wear) of the elastic material. From this point of view, in step S5 according to the present embodiment, when the volume change of the voids 15 is equal to or less than the second threshold value, it may be evaluated that the performance of the elastic material can be good.

The second threshold value can be set as appropriate according to, for example, various performances (performance related to wear in this embodiment) required for the elastic material. The second threshold of the embodiment is set to 1.0 to 3.0 (2.0 in this embodiment).

In step S5, when the volume change of the voids 15 is equal to or less than the second threshold value (2.0 in this embodiment) ("Yes" in step S5), the performance of the elastic material is evaluated to be good. In this case, a product (for example, a tire) using the elastic material (rubber) is designed and manufactured (step S6). This makes it possible to reliably manufacture products with excellent performance (in this embodiment, performance related to wear).

On the other hand, in step S5, when the volume change of the voids 15 is larger than the second threshold value (2.0 in this embodiment) ("No" in step S5), it is evaluated that the performance of the elastic material is not good. In this case, a new elastic material with a different composition is produced (step S7), and step S1 to step S5 are carried out again. This makes it possible to reliably produce elastic materials with excellent performance (in this example, performance related to wear).

In this embodiment, the performance related to wear (wear resistance) was evaluated, but the present disclosure is not limited to such an embodiment. For example, the tear resistance and crack resistance of the elastic material may be evaluated based on the volume change of the voids 15.

While the particularly preferable embodiments in accordance with the present disclosure have been described in detail, the present disclosure is not limited to the illustrated embodiments, but can be modified and carried out in various aspects within the scope of the disclosure.

Working Example

The wear resistance performance of elastic materials A to C was evaluated based on each volume change which was measured according to the method of the present disclosure. Furthermore, pneumatic tires with tread portions made of the above elastic materials A to C were prepared, and their tread wear resistance was evaluated by an actual vehicle running test. Then, the correlation between the evaluation of the wear resistance performance by the present disclosure and the evaluation of the wear resistance performance by the actual vehicle running test was verified (Example).

For comparison, the wear resistance performance of the elastic materials A to C was evaluated using a Ramborn tester, and then the correlation between the results and the evaluation of wear resistance performance by the actual vehicle running test was verified (comparative example).

The reagents used are as follows.
1. Polymer (1): (one modified group)
2. Polymer (2): (two modified groups; different amount of monomer in polymer (1))
3. Polymer (3): (three modified groups; different amount of monomer in polymer (1))
4. SBR: SPRINTAN SLR6430 made by STYRON
5. BR: BR150B manufactured by Ube Industries, Ltd.
6. Denaturant: 3-(N, N-dimethylaminopropyl) trimethoxysilane manufactured by Azumax Co., Ltd.
7. Anti-aging agent: Nocrack 6C (N-1,3-dimethylbutyl-N'-phenyl-p-phenylenediamine) manufactured by Ouchi Shinko Kagaku Kogyo Co., Ltd.
8. Stearic acid: Stearin manufactured by NOF CORPORATION
9. Zinc oxide: Ginrei R manufactured by Toho Zinc Co., Ltd.
10. Aromatic oil: Diana Process AH-24 manufactured by Idemitsu Kosan Co., Ltd.
11. Wax: Sunknock wax manufactured by Ouchi Shinko Kagaku Kogyo Co., Ltd.
12. Sulfur: Powdered sulfur manufactured by Tsurumi Chemical Co., Ltd.
13. Vulcanization accelerator (1): Noxeller CZ manufactured by Ouchi Shinko Kagaku Kogyo Co., Ltd.
14. Vulcanization accelerator (2): Noxeller D manufactured by Ouchi Shinko Kagaku Kogyo Co., Ltd.
15. Silica: Ultra Jill VN3 made by Degussa
16. Silane Coupling Agent: Si69 from Degussa
17. Carbon Black: Dia Black LH (N326, N2SA: 84m$^2$/g) manufactured by Mitsubishi Chemical Corporation The monomers and polymers (1) to (3) were synthesized by the same procedures as that described in "Examples" of Patent Document, Japanese Unexamined Patent Application Publication 2017-83182. The test methods are as follows.

Measurement of Volume Change of Voids:

Three columnar specimens made of the elastic materials A to C with a diameter of 20 mm and an axial length of 1 mm were prepared. Then, strain (tensile strain) was applied to each test piece according to the procedure shown in FIG. 3. Then, the projected images of each test piece were obtained at the first time when the strain reaches the first threshold value (0.2) and at the second time after a predetermined time (500 seconds) has elapsed from the first time. Then, according to the procedure shown in FIG. 5, the ratio Vt/V0 of the volume Vt of the voids at the second time to the volume V0 of the voids at the first time was obtained as the volume change of the voids. The smaller the volume change of the voids (value of the ratio Vt/V0), the better the wear resistance.

Ramborn Test:

The amount of wear of the elastic materials A to C was measured using a Ramborn type wear tester under the conditions of room temperature, load 1.0 kgf, and slip ratio 30%, and the reciprocal of the amounts were calculated. The results are shown in Table 1 using an index with the value of the elastic material A as 100, and the larger the value, the better the wear resistance performance.

Actual Vehicle Running Test:

Three kinds of pneumatic tires of size 195/65R15 with tread portions made of the elastic materials A to C were prepared, respectively. Each tire was mounted on a Japanese FF vehicle, and a groove depth of the tread portion at a mileage of 8000 km was measured. Then, the mileage per 1 mm of wear on the tread portion was calculated. The test results are shown in Table 1 using an index with the value of the elastic material A as 100, and the larger the value, the better the wear resistance.

Table 1 shows the test results.

TABLE 1

| | Elastic materials | A | B | C |
|---|---|---|---|---|
| Composition (mass) | BR | 20 | 20 | 20 |
| | Polymer (1) | 52 | — | — |
| | Polymer (2) | — | 52 | — |
| | Polymer (3) | — | — | 52 |
| | SBR | 28 | 28 | 28 |
| | Silica | 71 | 71 | 71 |
| | Silane Coupling Agent | 6 | 6 | 6 |
| | Carbon Black | 5 | 5 | 5 |
| | Aromatic oil | 21 | 21 | 21 |
| | Stearic acid | 2 | 2 | 2 |
| | Zinc oxide | 3 | 3 | 3 |
| | Anti-aging agent | 1 | 1 | 1 |
| | Wax | 1 | 1 | 1 |
| | Sulfur | 1.5 | 1.5 | 1.5 |
| | Vulcanization accelerator (1) | 1 | 1 | 1 |
| | Vulcanization accelerator (2) | 1 | 1 | 1 |
| Example | Volume change of voids (Vt/V0) | 1.52 | 1.35 | 1.24 |
| Comparative example | Ramborn wear test (index) | 100 | 102 | 102 |
| | Actual vehicle driving test (index) | 100 | 111 | 117 |

As a result of the test, as is clear from Table 1, the method of the example had a better correlation with the actual vehicle running test than the comparative example, and the performance of the elastic materials could be predicted (evaluated). Further, in the example, the elastic materials B and C which have the volume changes of voids being equal to or less than the second threshold value (1.5) showed significantly excellent in the actual vehicle running test as compared with the elastic material A which have the volume change of voids being larger than the second threshold value. As described above, the present disclosure was able to predict various performances of elastic materials with high accuracy.

The following clauses are disclosed regarding the above-described embodiments.

[Clause 1]

A performance evaluation method for elastic material including rubber or elastomer, the method comprising:
  a step of applying a strain to a test piece made of the elastic material to form at least one void inside the test piece;
  a step of obtaining projected images of the test piece by irradiating the test piece with X-rays at a plurality of times after the at least one void is formed; and
  a step of obtaining a volume change of the at least one void between the plurality of times based on the projected images, as one of indexes of performance.

[Clause 2]

The performance evaluation method according to clause 1, wherein the plurality of times comprises
  a first time when a strain given to the test piece reaches a predetermined first threshold value, and
  a second time after a predetermined time has elapsed from the first time.

[Clause 3]

The performance evaluation method according to clause 2, wherein the predetermined time is in a range from 100 to 1200 seconds.

[Clause 4]
The performance evaluation method according to clause 2 or 3, wherein
the first threshold value is equal to or more than 0.2.

[Clause 5]
The performance evaluation method according to any one of clauses 2 to 4, wherein
the step of obtaining a volume change obtains a ratio Vt/V0 of a volume Vt of the at least one void at the second time to a volume V0 of the at least one void at the first time, as the volume change.

[Clause 6]
The performance evaluation method according to any one of clauses 1 to 5, further comprising a step of evaluating the performance of the elastic material based on the volume change.

[Clause 7]
The performance evaluation method according to clause 6, wherein
the evaluation step comprises
a step of comparing the volume change with a predetermined second threshold value, and
a step of determining that the performance of the elastic material is good when the volume change is equal to or less than the second threshold value.

[Clause 8]
The performance evaluation method according to clause 7, wherein
the second threshold value is in a range from 1.0 to 3.0.

[Clause 9]
The performance evaluation method according to any one of clauses 1 to 8, wherein
the strain is a tensile strain.

[Clause 10]
The performance evaluation method according to any one of clauses 1 to 9, wherein
the step of obtaining projected images uses an imaging device that comprises a phosphor for converting X-rays into visible light, and
a decay time of the phosphor is equal to or less than 100 ms.

[Clause 11]
The performance evaluation method according to any one of clauses 1 to 10, wherein
the elastic material is rubber obtained using one or more kinds of conjugated diene compounds.

[Clause 12]
The performance evaluation method according to clause 11, wherein
the rubber is a rubber for tires.

[Clause 13]
The performance evaluation method according to any one of clauses 1 to 12, wherein
the X-rays have brightness equal to or more than $10^{10}$ (photons/s/mrad$^2$/mm$^2$/0.1%bw).

The invention claimed is:

1. A performance evaluation method for elastic material including rubber or elastomer, the method comprising:
a step of applying a strain to a test piece made of the elastic material to form at least one void inside the test piece;
a step of obtaining projected images of the test piece by irradiating the test piece with X-rays at a plurality of times after the at least one void is formed; and
a step of obtaining a volume change of the at least one void between the plurality of times based on the projected images, as one of indexes of performance,
wherein the plurality of times comprises:
a first time when a strain given to the test piece reaches a predetermined first threshold value; and
a second time after a predetermined time has elapsed from the first time.

2. The performance evaluation method according to claim 1, wherein the predetermined time is in a range from 100 to 1200 seconds.

3. The performance evaluation method according to claim 1, wherein the first threshold value is equal to or more than 0.2.

4. The performance evaluation method according to claim 1, wherein the step of obtaining a volume change obtains a ratio Vt/V0 of a volume Vt of the at least one void at the second time to a volume V0 of the at least one void at the first time, as the volume change.

5. The performance evaluation method according to claim 1, further comprising a step of evaluating the performance of the elastic material based on the volume change.

6. The performance evaluation method according to claim 5, wherein the evaluation step comprises:
a step of comparing the volume change with a predetermined second threshold value; and
a step of determining that the performance of the elastic material is good when the volume change is equal to or less than the second threshold value.

7. The performance evaluation method according to claim 6, wherein the second threshold value is in a range from 1.0 to 3.0.

8. The performance evaluation method according to claim 1, wherein the strain is a tensile strain.

9. The performance evaluation method according to claim 1,
wherein the step of obtaining projected images uses an imaging device that comprises a phosphor for converting X-rays into visible light, and
wherein a decay time of the phosphor is equal to or less than 100 ms.

10. The performance evaluation method according to claim 1, wherein the elastic material is rubber obtained using one or more kinds of conjugated diene compounds.

11. The performance evaluation method according to claim 10, wherein the rubber is a rubber for tires.

12. The performance evaluation method according to claim 1, wherein the X-rays have brightness equal to or more than $10^{10}$ (photons/s/mrad$^2$/mm$^2$/0.1% bw).

13. A performance evaluation method for elastic material including rubber or elastomer, the method comprising:
a step of applying a strain to a test piece made of the elastic material to form at least one void inside the test piece;
a step of obtaining projected images of the test piece by irradiating the test piece with X-rays at a plurality of times after the at least one void is formed;
a step of obtaining a volume change of the at least one void between the plurality of times based on the projected images, as one of indexes of performance;
a step of evaluating the performance of the elastic material based on the volume change,
wherein the evaluation step comprises:
a step of comparing the volume change with a predetermined second threshold value; and
a step of determining that the performance of the elastic material is good when the volume change is equal to or less than the second threshold value.

* * * * *